(12) United States Patent
Vogt et al.

(10) Patent No.: US 9,797,791 B2
(45) Date of Patent: Oct. 24, 2017

(54) MULTI-AXIS FORCE SENSING SOFT ARTIFICIAL SKIN

(71) Applicant: PRESIDENT AND FELLOWS OF HARVARD COLLEGE, Cambridge, MA (US)

(72) Inventors: Daniel Vogt, Cambridge, MA (US); Yong-Lae Park, Medford, MA (US); Robert J. Wood, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 192 days.

(21) Appl. No.: 14/438,792

(22) PCT Filed: Oct. 22, 2013

(86) PCT No.: PCT/US2013/066034
§ 371 (c)(1),
(2) Date: Apr. 27, 2015

(87) PCT Pub. No.: WO2014/066300
PCT Pub. Date: May 1, 2014

(65) Prior Publication Data
US 2015/0292968 A1    Oct. 15, 2015

Related U.S. Application Data

(60) Provisional application No. 61/719,398, filed on Oct. 27, 2012.

(51) Int. Cl.
*G01L 1/02* (2006.01)
*G01L 5/08* (2006.01)
(Continued)

(52) U.S. Cl.
CPC ........... *G01L 5/161* (2013.01); *G01L 1/02* (2013.01); *G01L 1/20* (2013.01); *A61B 2562/0261* (2013.01); *A61B 2562/164* (2013.01)

(58) Field of Classification Search
USPC .................................. 73/802.681, 862.581
See application file for complete search history.

(56) References Cited

U.S. PATENT DOCUMENTS 3,304,528 A    9/1967  Anderson et al.
3,789,511 A    2/1974  Groom et al.
(Continued)

FOREIGN PATENT DOCUMENTS

JP    H01-103281 A    4/1989
JP    H0388106 U    9/1991
(Continued)

OTHER PUBLICATIONS

Park et al., "Soft Artificial Skin with Multi-Modal Sensing Capability Using Embedded Liquid Conductors", IEEE, pp. 81-84, 2011.
(Continued)

*Primary Examiner* — Clayton E Laballe
*Assistant Examiner* — Warren K Fenwick
(74) *Attorney, Agent, or Firm* — Nixon Peabody LLP; David S. Resnick; David F. Crosby

(57) ABSTRACT

A sensor including a layer having viscoelastic properties, the layer comprising a void, the void filled with a fluid; and optionally, a more rigid sensing element embedded within the layer. When a force is applied to a surface of the sensor, the shape of the void changes, causing the electrical resistance of the fluid in the void to change. When included, the more rigid sensing element can bear upon the void to cause the electrical resistance of the fluid in the void to change. A direction and intensity of the force can be determined by (Continued)

measuring the change of the electrical resistance of different voids positioned about the sensing element. The layer can be an elastomer, preferably silicone rubber. The fluid can be a conductive liquid, preferably Eutectic Gallium Indium. The sensing element can be plastic and can have a "Joystick" shape. The voids can take the form of channels or microchannels having a predefined pattern and/or shape.

31 Claims, 7 Drawing Sheets

(51) Int. Cl.
*G01L 7/00* (2006.01)
*G01L 5/16* (2006.01)
*G01L 1/20* (2006.01)

(56) References Cited

U.S. PATENT DOCUMENTS

| | | | |
|---|---|---|---|
| 4,014,217 A | 3/1977 | Lagasse et al. | |
| 4,492,949 A | 1/1985 | Peterson et al. | |
| 4,547,668 A | 10/1985 | Tsikos | |
| 4,570,354 A | 2/1986 | Hindes | |
| 4,588,348 A | 5/1986 | Beni et al. | |
| 4,668,861 A | 5/1987 | White | |
| 4,682,608 A * | 7/1987 | De Rigal | A61B 5/0051 600/587 |
| 5,313,840 A | 5/1994 | Chen et al. | |
| 5,333,217 A | 7/1994 | Kossat | |
| 5,341,687 A | 8/1994 | Stan | |
| 5,442,799 A | 8/1995 | Murakami et al. | |
| 5,553,500 A | 9/1996 | Grahn et al. | |
| 5,610,528 A | 3/1997 | Neely et al. | |
| 5,672,979 A | 9/1997 | Christopher | |
| 5,828,798 A | 10/1998 | Hopenfeld | |
| 5,886,615 A * | 3/1999 | Burgess | H01H 1/029 200/86 R |
| 5,917,165 A | 6/1999 | Platt et al. | |
| 5,959,863 A | 9/1999 | Hoyt et al. | |
| 6,071,819 A * | 6/2000 | Tai | B81B 7/0077 438/694 |
| 6,414,674 B1 | 7/2002 | Kamper et al. | |
| 6,825,539 B2 * | 11/2004 | Tai | G01M 9/065 257/417 |
| 6,915,701 B1 | 7/2005 | Tarler | |
| 6,951,143 B1 | 10/2005 | Adderton et al. | |
| 6,953,982 B1 * | 10/2005 | Tai | B81B 7/0077 257/522 |
| 7,295,724 B2 | 11/2007 | Wang et al. | |
| 7,500,399 B2 | 3/2009 | Cheng et al. | |
| 7,658,119 B2 | 2/2010 | Loeb et al. | |
| 7,815,998 B2 | 10/2010 | Simpson et al. | |
| 7,854,173 B2 | 12/2010 | Cheng et al. | |
| 7,878,075 B2 * | 2/2011 | Johansson | B25J 13/084 73/862.046 |
| 8,033,189 B2 | 10/2011 | Hayakawa et al. | |
| 8,316,719 B2 | 11/2012 | Majidi et al. | |
| 2005/0076715 A1 | 4/2005 | Kuklis et al. | |
| 2005/0160827 A1 | 7/2005 | Zdeblick et al. | |
| 2005/0261632 A1 | 11/2005 | Xu | |
| 2008/0087069 A1 | 4/2008 | Renken et al. | |
| 2008/0087105 A1 | 4/2008 | Renken et al. | |
| 2008/0108122 A1 | 5/2008 | Paul et al. | |
| 2009/0098521 A1 * | 4/2009 | Kuo | G09B 23/30 434/267 |
| 2009/0272201 A1 * | 11/2009 | Loeb | G01L 5/228 73/862.041 |
| 2010/0132476 A1 | 6/2010 | Ching-Hsiang et al. | |
| 2011/0096327 A1 | 4/2011 | Papautsky et al. | |
| 2011/0132871 A1 | 6/2011 | White et al. | |
| 2011/0193363 A1 | 8/2011 | Nishiwaki | |
| 2013/0170218 A1 * | 7/2013 | Wolk | G02B 6/0036 362/296.01 |
| 2013/0312541 A1 * | 11/2013 | Majidi | G01B 7/18 73/862.454 |
| 2014/0238153 A1 * | 8/2014 | Wood | G06F 3/011 73/862.627 |
| 2015/0088043 A1 * | 3/2015 | Goldfield | A61F 5/01 602/6 |

FOREIGN PATENT DOCUMENTS

| | | |
|---|---|---|
| JP | 3041795 U | 10/1997 |
| JP | H11-166804 A | 6/1999 |
| JP | 2004-101322 A | 4/2004 |
| JP | 2006258076 A | 9/2006 |
| JP | 2006318175 A | 11/2006 |
| WO | 0188935 A1 | 11/2001 |
| WO | 2007089158 A1 | 8/2007 |
| WO | 2012050938 A2 | 4/2012 |
| WO | 2013044226 A2 | 3/2013 |

OTHER PUBLICATIONS

Park et al., "Design and Fabrication of Soft Artificial Skin Using Embedded Microchannels and Liquid Conductors", IEEE Sensors Journal, vol. 12, No. 8, pp. 2711-2718, 2012.
Barlian et al., "Design and characterization of microfabricated piezoresistive floating element-based shear stress sensors," Sensor Actuator A-Phys., 134(1):77-87 (2007).
Hsieh et al., "A contact-type piezoresistive micro-shear stress sensor for above-knee prosthesis application," J Microelectromech S., 121-7 (2011).
Jiang et al., "A flexible mems technology and its first application to shear stress sensor skin," MEMS '97, Proc IEEE, 10th Annual International Workshop., 465-70 (1997).
Majidi et al., "A non-differential elastomer curvature sensor for softer-than-skin electronics," Smart Mater Struct., 20:105017 (7 pages) (2011).
Marculescu et al., "Electronic textiles: a platform for pervasive computing" Proc of IEEE., 91(12):1995-2018 (2003).
Okamura et al., "Feature detection for haptic exploration with robotic fingers," Int J Robot. Res., 20(12):925-38 (2001).
Park et al., "Bio-inspired active soft orthotic device for ankle foot pathologies," Proc. IEEE/RSJ Int Conf Intell Rob Syst., p. 4488-95 (2011).
Park et al., "Hyperelastic pressure sensing with a liquid-embedded elastomer," J Micromech Microeng., 20:125029 (6 pages) (2010).
Puangmali et al., "State-of-the-art in force and tactile sensing for minimally invasive surgery," Sensors Journal, IEEE., 8(4):371-81 (2008).
Tajima et al., "Development of soft and distributed tactile sensors and the application to a humanoid robot," Adv Robotics., 16(4):381-97 (2002).
Xu et al., "IC-integrated flexible shear-stress sensor skin," J Microelectromech S., 740-7 (2003).
Alirezaei et al., "A highly stretchable tactile distribution sensor for smooth surfaced humanoids", Humanoid Robots, 2007 7th IEEE-RAS International Conference on. IEEE, (2007).
Cheng et al., "The development of a highly twistable tactile sensing array with stretchable helical electrodes," Sensors and Actuators A 166:226-233 (2011). Available online Dec. 16, 2009.
Chigusa et al., "Large Area Sensor Skin based on Two-Dimensional Signal Transmission Technology", Second joint EuroHaptics Conference and Symposium on Haptic Interfaces for Virtual Environment and Teleoperator Systems (2007).
Cotton et al., "A Multifunctional Capacitive Sensor for Stretchable Electronic Skins", IEEE Sensors J. 9(12):2008-2009 (2009).
Dickey et al., "Eutectic Gallium-Indium (EGaIn): A Liquid Metal Alloy for the Formation of Stable Structures in Microchannels at Room Temperature," Adv. Funct. Mater. 18:1097-1104 (2008).
Duffy et al., "Rapid Prototyping of Microfluidic Systems in Poly(dimethylsiloxane)", Anal. Chem. 70:4974-4984 (1998).
Herr et al., "New horizons for orthotic and prosthetic technology: artificial muscle for ambulation", Smart Structures and Materials

(56) References Cited

OTHER PUBLICATIONS

2004: Electroactive Polymer Actuators and Devices, edited by Joseph Bar-Cohen, Proceedings of SPIE vol. 5385 (SPIE, Bellingham, WA, 2004).
Hoshi et al., "Robot Skin Based on Touch-Area-Sensitive Tactile Element", Proceedings of the 2006 IEEE International Conference on Robotics and Automation (Orlando, FL, May 2006).
Khang et al., "A Stretchable Form of Single-Crystal Silicon for High-Performance Electronics on Rubber Substrates", Science 311:208-212 (2006).
Kim et al., "A multiaxial stretchable interconnect using liquid-alloy-filled elastomeric microchannels", Applied Physics Letters 92:011904 (2008).
Kim et al., "Stretchable and Foldable Silicon Integrated Circuits", Science 320:507-511 (2008).
Kim et al., "Fabrication of microchannel containing nanopillar arrays using micromachined AAO (anodic aluminum oxide) mold", Microelectronic Engineering 84:1532-1535 (2007).
Kirchner et al., "Capacitive sensor for object ranging and material type identification," Sensors and Actuators A 148:96-104 (2008).
Kramer et al., "Wearable Tactile Keypad with Stretchable Artificial Skin", 2011 IEEE International Conference on Robotics and Automation (Shanghai, May 9-13, 2011).
Lacasse et al., "Characterization of the Electrical Resistance of Carbon-Black-Filled Silicone: Application to a Flexible and Stretchable Robot Skin" 2010 IEEE International Conference on Robotics and Automation, Achorage Convention District (Anchorage, AK, May 3-8, 2010).
Lorussi et al., "Strain Sensing Fabric for Hand Posture and Gesture Monitoring," IEEE Transactions on Information Technology in Biomedicine 9(3):372-381 (2005).
Menon et al., "Maskless lithography", Materls Today 8:26-33 (2005).
Noda et al., "Stretchabe liquid tactile sensor for robot-joints", 2010 IEEE International Conference on Robotics and Automation, Anchorage Convention District, (Anchorage, AK, May 3-8, 2010).
Park et al., "Exoskeletal Force-Sensing End-Effectors With Embedded Optical Fiber-Bragg-Grating Sensors" IEEE Transactions on Robotics 25(6):1319-1331 (2009).
Pique et al., "Direct writing of electronic and sensor materials using a laser transfer technique", J. Mater. Res. 15(9):1872-1875 (2000).
Quake et al., "From Micro- to Nanofabrication with Soft Materials", Science 290(5496):1536-1540 (2000).
Rogers et al., "A curvy, stretchy future for electronics". Proc. Natl. Acad. Sci. USA 106(27):10875-10876 (2009).
So et al., "Reversibly Deformable and Mechanically Tunable Fluidic Antennas", Adv. Fund. Mater. 19:3632-3637 (2009).
Stirling et al., "Applicability of Shape Memory Alloy Wire for an Active, Soft Orthotic", Journal of Materials Engineering and Performance 20(4-5):658-662 (2011).
Takei et al., "Nanowire active-matrix circuitry for low-voltage macroscale artificial skin", Nature Materials 9:821-826 (2010).
Tseng et al., "A slow-adapting microfluidic-based tactile sensor", J. Micromech. Microeng. 19:085002 (2009).
Ulmen et al., "A Robust, Low-Cost and Low-Noise Artificial Skin for Human-Friendly Robots," 2010 IEEE International Conference on Robotics and Automation, Anchorage Convention District (Anchorage, AK, May 3-8, 2010).
Unger et al., "Monolithic Microfabricated Valves and Pumps by Multilayer Soft Lithography", Science 288:113-116 (2000).
Ventrelli et al., "Development of a stretchable skin-like tactile sensor based on polymer composites" International Conference of Robotics and Biomimetics (Guilin, China, Dec. 19-23, 2009).
Vogt et al., "Multi-axis force sensing in a soft artificial skin", IEEE (2012).
Wettels et al., "Biomimetic Tactile Sensor Array", Advanced Robotics 22:829-849 (2008).
Whitney, "The measurement of changes in human limb-volume by means of a mercury-in-rubber strain gauge", Proceedings of Phys. Soc. 109:5P-6P (1949).
Xia et al., "Soft Lithography", Annu. Rev. Mater. Sci. 28:153-184 (1998).
Yamada et al., "Artificial Finger Skin having Ridges and Distributed Tactile Sensors used for Grasp Force Control," Proceedings of the 2001 IEEE/RSJ International Conference on Intelligent Robots and Systems (Maui, HI, Oct. 29-Nov. 3, 2001).
Yoshikai et al., "Development of Soft Stretchable Knit Sensor for Humanoids' Whole-body Tactile Sensibility", 9th IEEE-RAS International Conference on Humanoid Robots (Paris, France, Dec. 7-10, 2009).

* cited by examiner

MULTI-AXIS FORCE SENSING SOFT ARTIFICIAL SKIN

CROSS-REFERENCE TO RELATED APPLICATIONS

This application is a 35 U.S.C. §371 National Phase Entry Application of International Application No. PCT/US2013/066034 filed Oct. 22, 2013, which designates the U.S., and which claims benefit under 35 U.S.C. §119(e) of U.S. Provisional Application No. 61/719,398 filed Oct. 27, 2012, the contents of each of which are hereby incorporated by reference in their entirety.

TECHNICAL FIELD

The present invention relates generally to a flexible substrate that includes one or more rigid sensing elements embedded therein and one or more microchannels containing a conductive fluid. The rigid sensing elements are stiffer than the flexible substrate and include a planar portion having a projection extending substantially perpendicular to the planar portion. In operation, when a force is applied to the flexible substrate, the rigid sensing element moves relative to the substrate and applies a force on one or more of the microchannels changing its cross-sectional dimension and the resistance of the conductive fluid. The change in electrical resistance allows the substrate to detect not only pressure perpendicular to the surface of the substrate, but also sliding (shear) forces parallel to the surface of the substrate.

BRIEF SUMMARY

Various sensors have been developed for applications in robotics, computer data input devices, the automobile industry and the medical industry.

For example, U.S. Pat. No. 4,492,949 to Peterson is directed to a tactile sensor with a top layer having a flexible, electrically-insulating material and a plurality of parallel flexible conductive rods; a bottom layer having an electrically-insulating material and a plurality of parallel conductive rods that extend at right angles to the conductive rods of the top layer; and an intermediate layer having resilient, electrically-insulating material in which is disposed a plurality of parallel conductive posts that extend perpendicularly to the plane of the three layers.

U.S. Pat. No. 5,313,840 to Chen is directed to a tactile shear sensor having an anisotropically conductive material disposed between a conductive cursor and an array of contacts.

U.S. Pat. No. 5,959,863 to Hoyt is directed to a multiple axis data input apparatus having a multiple axis joystick.

U.S. Pat. No. 6,951,143 to Adderton is directed to a three-axis sensor assembly that uses an elastomeric material.

U.S. Pat. No. 7,854,173 to Cheng is directed to a strain sensor having a conductive liquid, which may be made from a eutectic alloy of gallium, indium and tin provided within two substrates, which may be made from polydimethylsiloxane (PDMS).

U.S. Pat. No. 8,033,189 to Hayakawa is a directed to a robotic skin having tactile sensors on a base, a continuously formed first member on the sensors, projections tapered toward the sensors and a second member having a lower rigidity than the first member.

However, these known sensors are not particularly well adapted for measuring both pressure and shear stress and for use in a relatively flexible, stretchable material.

One object of the present invention is to provide a flexible and stretchable, multi-axis sensor.

BRIEF DESCRIPTION OF THE DRAWINGS

The accompanying drawings, which are incorporated into this specification, illustrate one or more exemplary embodiments of the inventions disclosed herein and, together with the detailed description, serve to explain the principles and exemplary implementations of these inventions. One of skill in the art will understand that the drawings are illustrative only, and that what is depicted therein may be adapted based on the text of the specification and the spirit and scope of the teachings herein.

In the drawings, where like reference numerals refer to like reference in the specification.

DETAILED DESCRIPTION

Figure 1:
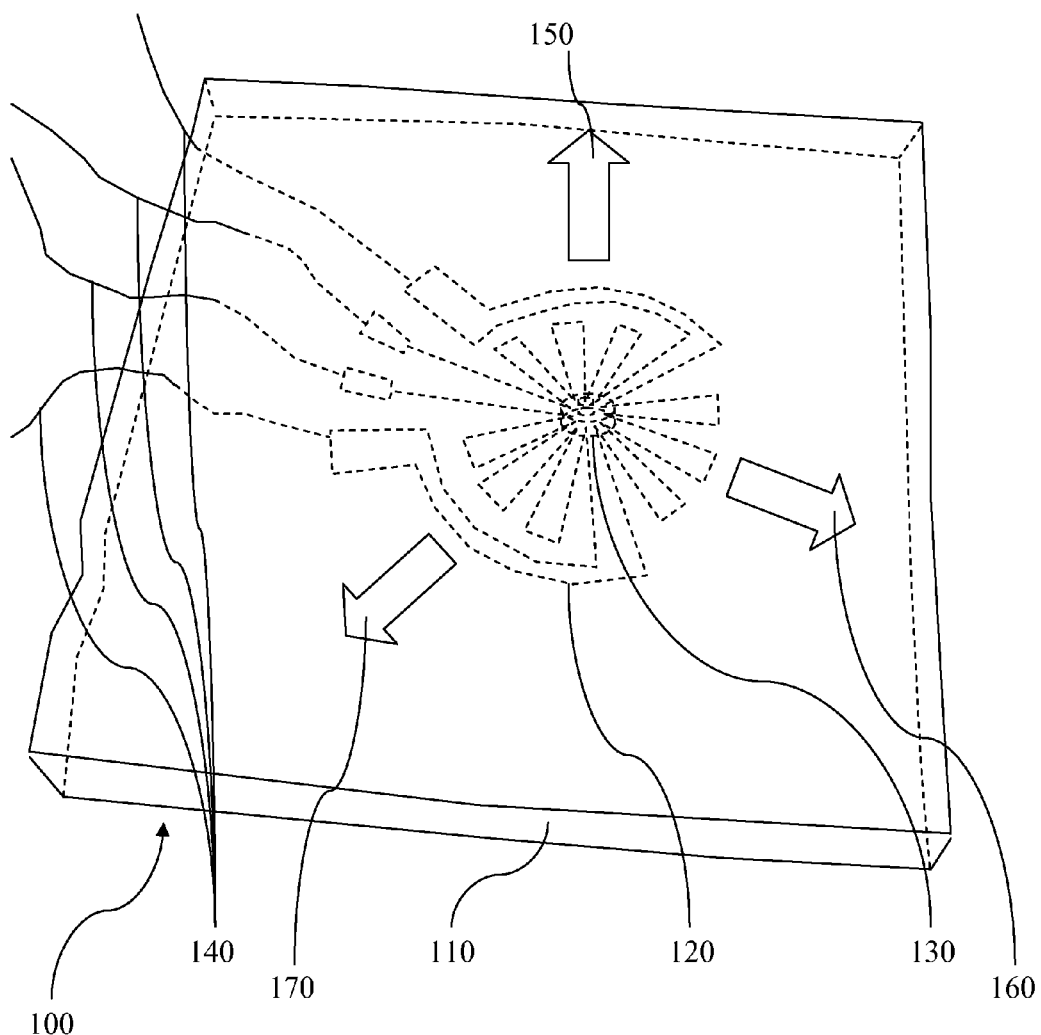
FIG. 1 is a general view of a shear and pressure sensor according to an embodiment of the invention.

It should be understood that this invention is not limited to the particular methodology, protocols, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities used herein should be understood as modified in all instances by the term "about."

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments of the aspects described herein, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to the invention, yet open to the inclusion of unspecified elements, whether essential or not.

As used herein the term "consisting essentially of" refers to those elements most useful for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Other than in the operating examples, or where otherwise indicated, all numbers expressing quantities used herein should be understood as modified in all instances by the term "about." The term "about" when used in connection with percentages may mean ±1%.

The singular terms "a," "an," and "the" include plural referents unless context clearly indicates otherwise. Similarly, the word "or" is intended to include "and" unless the context clearly indicates otherwise. Thus, for example, references to "the method" includes one or more methods, and/or steps of the type described herein and/or which will become apparent to those persons skilled in the art upon reading this disclosure and so forth.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

In accordance with one embodiment of the invention as shown in FIG. 1, the sensor 100 can measure loads along up to three axes (pressure and shear stress in two dimensions) on a surface of the sensor 100. The sensor 100 can include a polymer layer 110 having viscoelastic properties, such as an elastomer. The sensor 100 can include one or more channels filled with a fluid and a more rigid sensing element. For example, in one embodiment, the sensor 100 can include embedded micro-channels 120 filled with a conductive liquid 125, such as Eutectic Gallium Indium (EGaIn), and a more rigid 3 dimensional sensing element 130. The conductive liquid 125 can include, for example, one or more of mercury, gallium, indium, tin, nickel, copper and silver. The micro-channels can be connected to a sensing device, such as an ohmeter, via leads 140.

The more rigid sensing element 130 (FIG. 2A) can be formed of a material that is substantially more rigid than the polymer layer 110 that the sensor can be embedded within. The difference in rigidity between the polymer layer 110 and the sensor element 130 can be determined based on the desired sensitivity and the intended application of the sensor. Where a greater sensitivity to small changes of force is desired, a greater difference in rigidity can be provided.

In addition, the size and shape of the more rigid sensing element 130 can be configured to provide the desired direction of sensing and level of sensitivity. In accordance with one embodiment of the invention, the sensing element 130 can, for example, include a rod extending along an axis and the axis can extend substantially transverse to the direction of sensing. In this embodiment, when a shear force is applied to the surface of the polymer layer, the rod is caused to bear against one or more of the microchannels and cause a change in the resistance of the fluid contained therein. In further embodiments according to the invention, the sensing element 130 can extend in 3 dimensions to enable sensing in 2 or 3 dimensions. Different portions of the sensing element 130 can be positioned adjacent to separate or individual fluid containing microchannels 120 enable sensing in 2 or 3 dimensions. In accordance with some embodiments of the invention, the sensing element can have a shape that facilitates the detection of multi-axis force, that is, force in multiple directions.

Figure 2A:
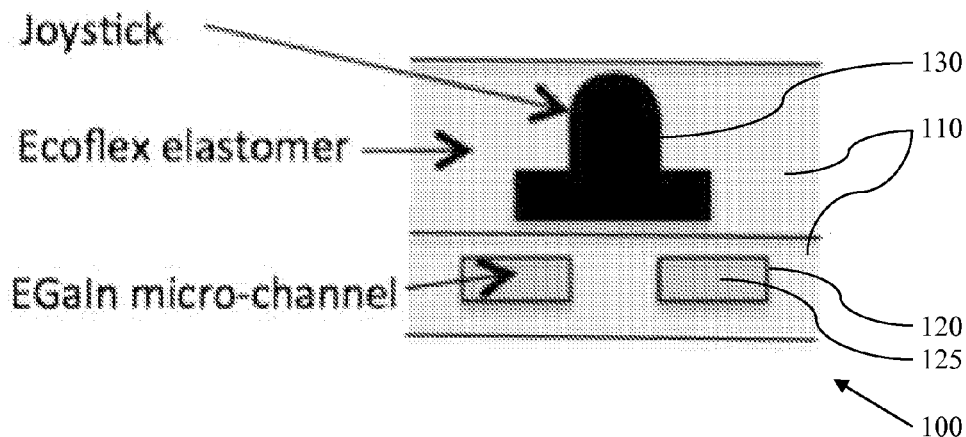
FIG. 2A is a cross section of different layers of a sensor according to an embodiment of the invention.
Figure 2B:
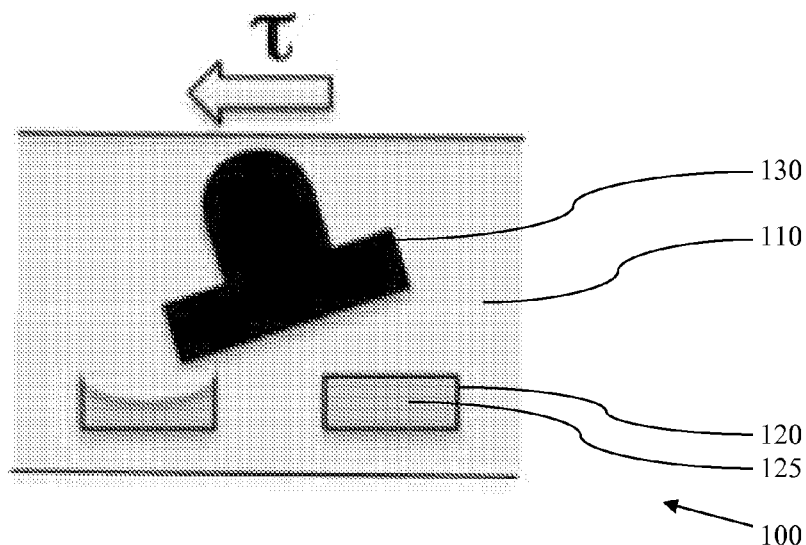
FIG. 2B is a cross section of a sensor according to an embodiment of the invention showing deformation of an EGaIn channel due to a shear stress $\tau$.

For example, in accordance with one embodiment of the invention as shown in FIGS. 2A and 2B, the sensing element 130 can have a planar portion and a transverse projecting portion extending transverse to the planar portion to form a joystick. In some embodiments, the polymer layer can extend a long a plane and the planar portion can lie in a plane parallel to the plane of the polymer layer with projecting portion extending substantially transverse to the plane of the polymer layer. The polymer layer can be provided with two or more microchannels positioned adjacent the planar portion of the sensing element 130, such that a force applied to the polymer layer causes sensing element 130 to move (e.g. rotate) within the polymer layer to bear upon and change the cross-sectional shape of (e.g., deform) at least one of the microchannels resulting in a change in electrical resistance through the channel. In this embodiment, a force applied transverse to the plane of the polymer layer can be transferred to the transverse projecting portion of the sensing element 130 and the planar portion of the joystick to cause changes (e.g., deformation) of two or more microchannels indicating a normal force or pressure on the polymer layer. And, a shear force applied along the plane of the polymer layer can cause the sensing element 130 to rotate and cause the planar portion to cause changes in deformation of two or more microchannels indicating a shear force along the plane of the polymer layer.

In accordance with the invention, the sensing element can include a lower portion having a width greater than a height and an upper portion having a height greater than a width, where the upper portion has a vertical axis that is parallel to or close to a vertical axis of the lower portion and where the upper and lower portion have horizontal cross sectional shapes that are circular, rounded, rectangular or polygonal. This shape can be characterized, for example, as a "Joystick" shape. The sensing element 130 can include a rigid plastic structure, for example, made using any suitable means including additive manufacturing methods such as a 3D printing, subtractive manufacturing methods such as machining, molding, casting, extrusion and the like. For example, in one embodiment, the sensing element 130 can be made using a 3D printer, such as the Connex 500, manufactured by Objet Geometries, Billerica, Mass. 01821, USA. The rigid plastic structure 130 may be embedded in material such as an elastomer. For example, in one embodiment, the rigid plastic structure 130 can be embedded in a silicone rubber layer, such as EcoFlex0030, manufactured by Smooth-On Inc., Easton, Pa. 18042, USA.

Figure 3:
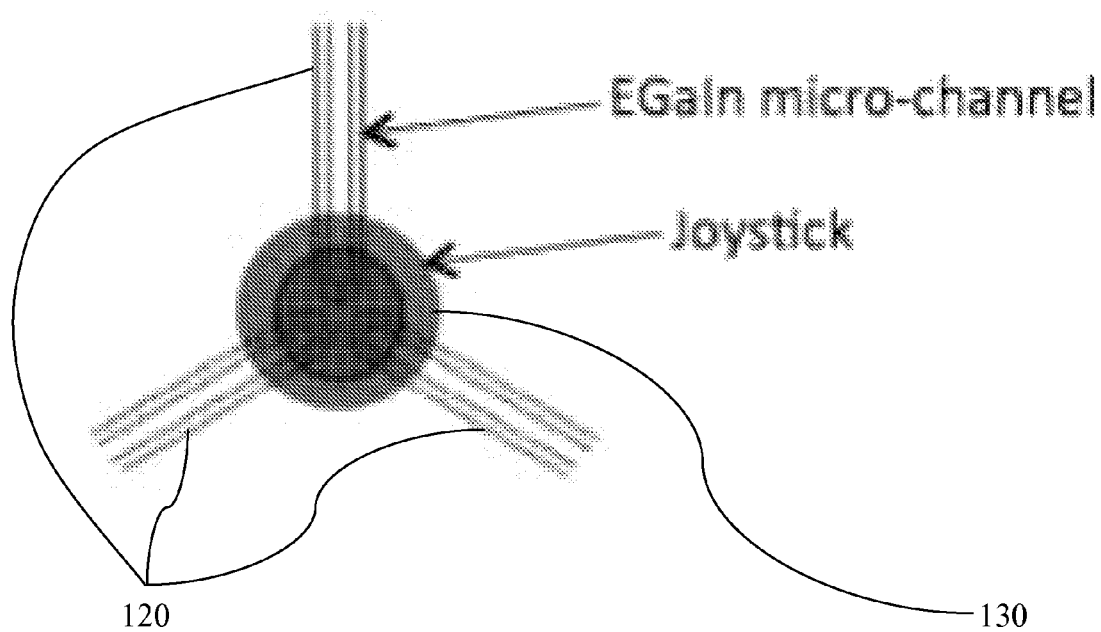
FIG. 3 is a top view of the micro-channel configuration according to an embodiment of the invention.

The sensor 100 can be made of two superposed layers such as that shown, for example, in FIG. 2A. The top layer can have a rigid plastic structure 130 made by a 3D printer, which can be embedded in an elastomer, such as EcoFlex0030. The bottom layer can contain EGaIn microchannels in a star configuration, such as that shown, for example, in FIG. 3. In one embodiment, three microchannels are separated by 120°, and follow a line so that they pass under the joystick and come back to the extremity. Although the minimum number of channels for measuring three-axis forces (shear force in x and y axes and surface pressure in z-axis) is three, any suitable number of channels may be used. For example, more than three channels can be used for higher accuracy and sensor redundancy. For example, four channels can be used with a 90° interval or eight channels can be used with 45° intervals.

When a normal force (pressure) is applied on the surface of the top layer, the joystick applies pressure on, for example, three channels resulting in increased electrical resistances of the three channels (FIG. 2A). With a shear force, the joystick will rotate and apply pressure on only, for example, one or two of the three microchannels (FIG. 2A), which also cause increased resistance of the deformed channels.

By monitoring the resistance changes of the three sensor signals generated by three microchannels, the direction of the load (x, y, or z axis) and its magnitude can be determined.

Figure 4:
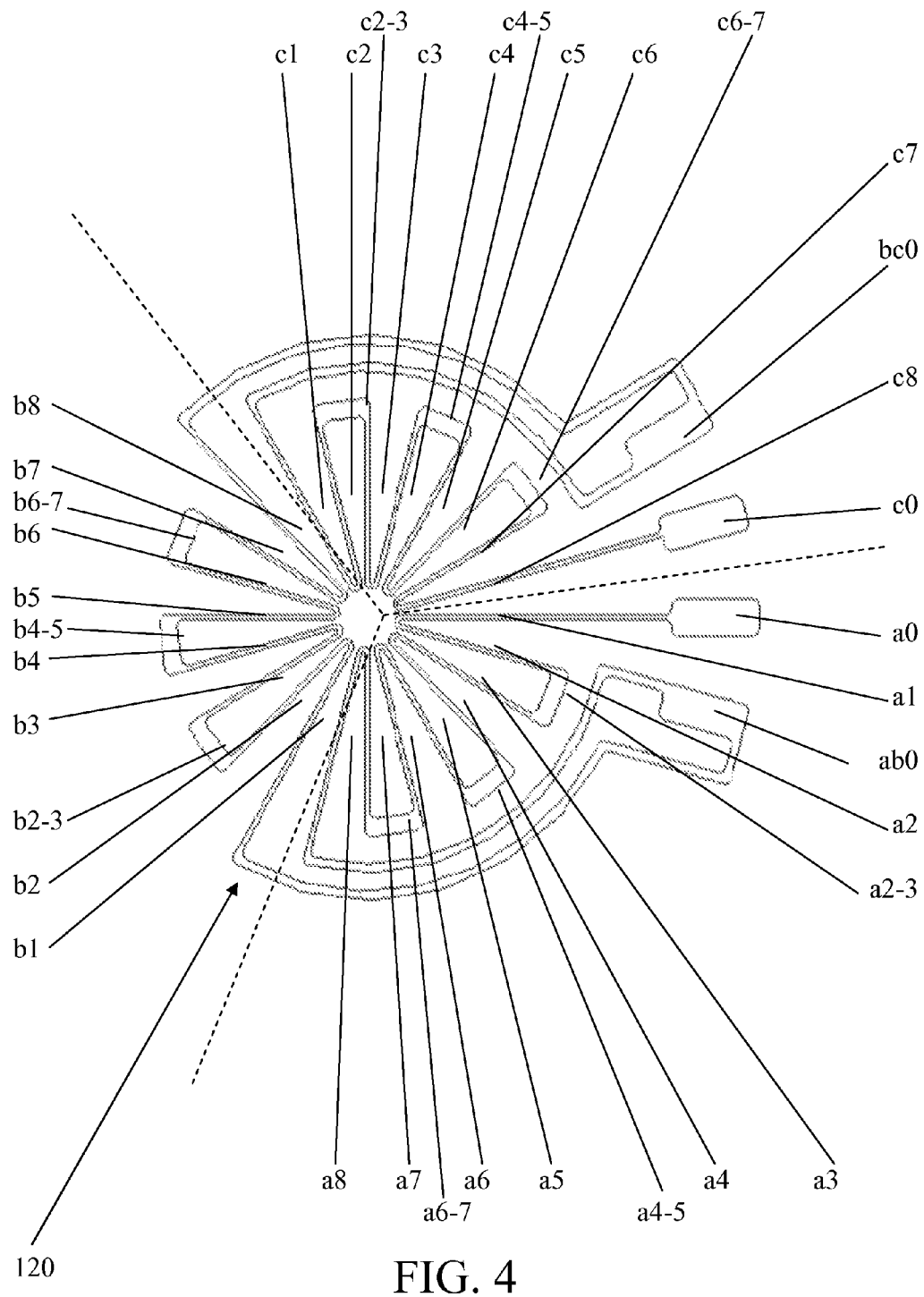
FIG. 4 is a top view of an embodiment of the invention having twenty-four microchannels.
Figure 5A:
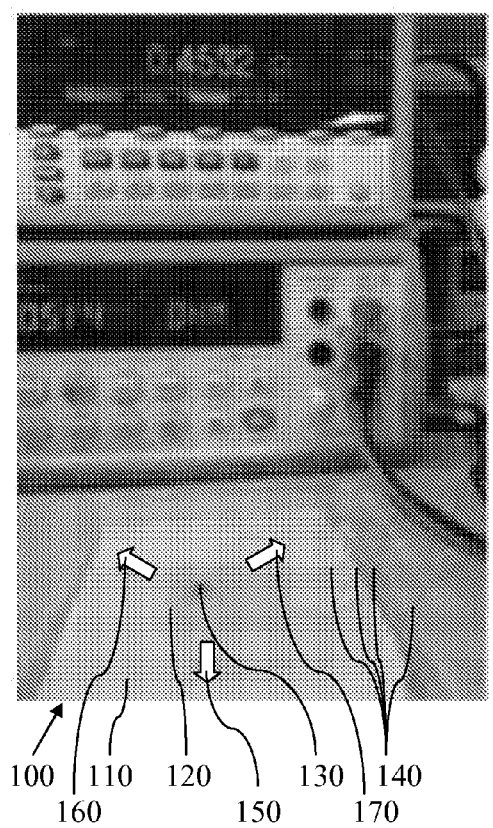
FIG. 5A is a perspective view of a sensor according to an embodiment of the invention where no stress is applied to the sensor.
Figure 5B:
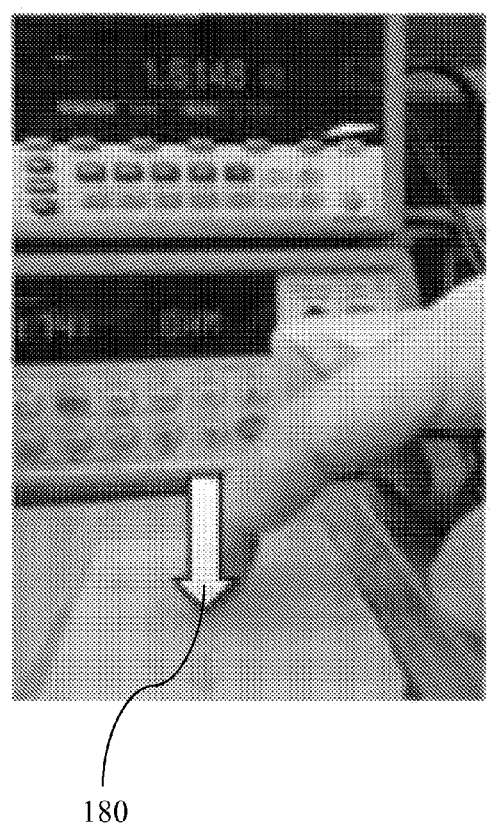
FIG. 5B is a perspective view of a sensor according to an embodiment of the invention where normal pressure is applied in a generally vertical direction with respect to the surface of the sensor.

FIG. 4 shows an example of channel design according to an embodiment of the invention. The channel can comprise a plurality of microchannels, and the microchannels can be continuously interconnected. The microchannels can be divided into three major channels (a, b, and c), where channel a is adapted to measure forces in direction 150 as shown in FIG. 1, FIG. 4, and FIG. 5A, where channel b is adapted to measure forces in direction 160 and where channel c is adapted to measure forces in direction 170. Each channel a, b, and c can have eight sub channels, e.g., a1, a2, a3, a4, a5, a6, a7, a8, b1, b2, b3, b4, b5, b6, b7, b8, c1, c2, c3, c4, c5, c6, c7 and c8, which makes the total number of channels around the joystick twenty-four. The subdivision of the microchannel increases the resolution of the shear force directions and the sensitivity.

A first channel pad area a0 can have a generally rectangular shape when viewed from above, which can be connected to microchannel a1, which extends toward a central axis of the microchannels and turns radially away from the central axis to form microchannel a2. The microchannels can be connected together and repeat the pattern of radiating back and forth about the central axis. The angle between any one of the microchannels a1, a2, a3, a4, a5, a6, a7, a8, b1, b2, b3, b4, b5, b6, b7, b8, c1, c2, c3, c4, c5, c6, c7 and c8 and the next adjacent microchannel can be about fifteen degrees (15°).

The pair of microchannels a2 and a3 can be linked by a broadened microchannel connector a2-a3, which can have a generally rectangular shape that is relatively smaller than the first channel pad area a0. Similarly, the pair of microchannels a4 and a5 can be linked by a broadened microchannel connector a4-a5, the pair of microchannels a6 and a7 can be linked by a broadened microchannel connector a6-a7, the pair of microchannels b2 and b3 can be linked by a broadened microchannel connector b2-b3, the pair of microchannels b4 and b5 can be linked by a broadened microchannel connector b4-b5, the pair of microchannels b6 and b7 can be linked by a broadened microchannel connector b6-b7, the pair of microchannels c2 and c3 can be linked by a broadened microchannel connector c2-c3, the pair of microchannels c4 and c5 can be linked by a broadened microchannel connector c4-c5 and the pair of microchannels c6 and c7 can be linked by a broadened microchannel connector c6-c7.

The pair of microchannels a8 and b1 can be linked by a broadened microchannel connector ab0, which can have a generally rectangular shape that is relatively the same size as the first channel pad area a0. Also, in this example, the broadened microchannel connector ab0 can be located on the same side of the embedded microchannels 120 as the first channel pad area a0 and can be connected to the pair of microchannels a8 and b1 with arc-shaped microchannels. In this example, the centerline of the broadened microchannel connector ab0 can be approximately parallel with the centerline of microchannel a2, and the centerline of the first channel pad area a0 and the centerline of the broadened microchannel connector ab0 can form an angle of about fifteen degrees (15°).

The pair of microchannels b8 and c1 can be linked by a broadened microchannel connector bc0, which can have a generally rectangular shape that is relatively the same size as the first channel pad area a0. Also, in this example, the broadened microchannel connector bc0 can be located on the same side of the embedded microchannels 120 as the first channel pad area a0 and can be connected to the pair of microchannels b8 and c1 with arc-shaped microchannels. In this example, the centerline of the broadened microchannel connector bc0 can be approximately parallel with the centerline of microchannel c7.

Microchannel c8 can terminate in a second channel pad area c0, which can be similar to the first channel pad area a0, and the centerline of the second channel pad area c0 and the centerline of the broadened microchannel connector bc0 can form an angle of about fifteen degrees (15°).

The first channel pad area a0, the broadened microchannel connector ab0, the broadened microchannel connector bc0 and the second channel pad area c0 can be located near each other to facilitate connection to a meter, such as an ohmmeter, via leads 140, shown, for example, in FIG. 1 and FIG. 5A.

As shown, for example, in FIG. 5A-5B and FIG. 6A-6B, two ohmmeters are connected to two channels of an example of a sensor according to the present invention.

A pressure normal to the sensor's surface will create an approximately equal increase of resistance in, for example, three microchannels (FIG. 5A). For example, in FIG. 5A, no force is applied, and one channel has a reading of 0.4532 ohms, and the other channel has a reading of 0.514 ohms, which is a difference of about 0.061 ohms, and in FIG. 5B, a generally normal force is applied, and one channel has a reading of 1.6148 ohms, and the other channel has a reading of 1.741 ohms, which is a difference of about 0.126 ohms. That is, the difference between readings on the one channel and the other channel is relatively small (less than about 0.150 ohms) as compared to when a generally shear stress is applied (about 0.500 to 0.800 ohms), described below.

Figure 6A:
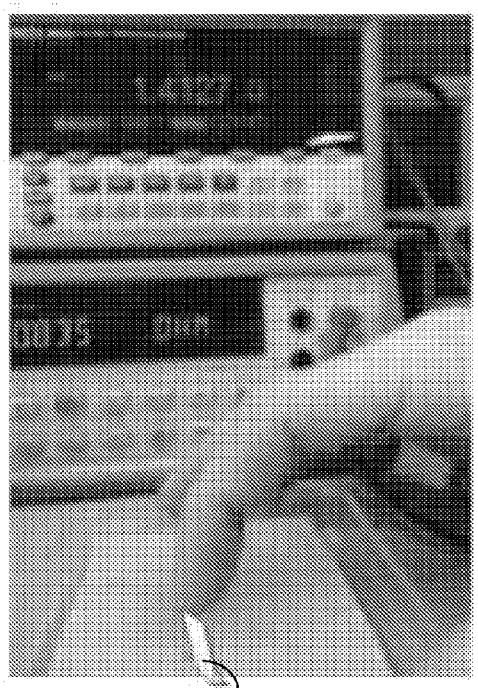
FIG. 6A is a perspective view of a sensor according to an embodiment of the invention where shear stress is applied in one generally horizontal direction.
Figure 6B:
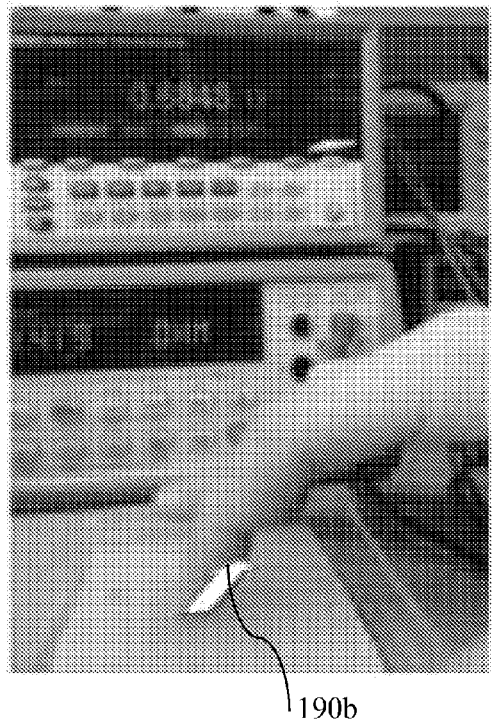
FIG. 6B is a perspective view of a sensor according to an embodiment of the invention where shear stress is applied in another generally horizontal direction.

A shear stress will create a non-uniform change of resistance in, for example, three microchannels (FIG. 6). This allows estimating the direction of the applied shear stress depending on the partition of the resistance change. For example, in FIG. 6A, a force is applied in one direction, and one channel has a reading of 1.4127 ohms, and the other channel has a reading of 0.835 ohms, which is a difference of about 0.578 ohms, and in FIG. 6B, a generally normal force is applied, and one channel has a reading of 0.6843 ohms, and the other channel has a reading of 1.419 ohms, which is a difference of about 0.735 ohms. That is, the difference between readings on the one channel and the other channel is relatively large (about 0.500 to 0.800 ohms) as compared to when a generally shear stress is applied (less than about 0.150 ohms), described above.

Figure 7A:
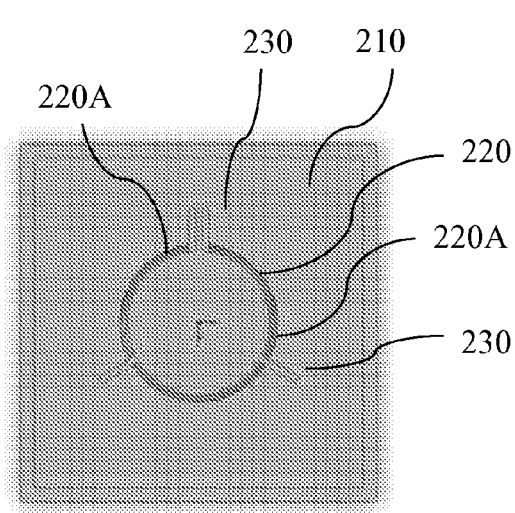
FIG. 7A is a general view of a sensor according to an embodiment of the invention where a rigid sensing element is not used.
Figure 7B:
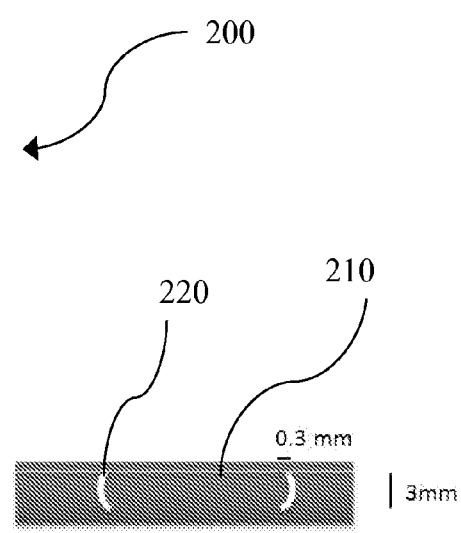
FIG. 7B is a cross section view of the sensor according to the embodiment of the invention shown in FIG. 7A.

In accordance with one embodiment of the invention as shown in FIGS. 7A and 7B, the sensor 200 can measure loads along up to two axes (shear stress in two dimensions) on a surface of the sensor 200. The sensor 200 can include a polymer layer 210 having viscoelastic properties, such as an elastomer. The sensor 200 can include one or more channels filled with a fluid without a more rigid sensing element as described elsewhere herein. For example, in one embodiment, the sensor 200 can include embedded microchannels 220 filled with a conductive liquid 225, such as Eutectic Gallium Indium (EGaIn), but no sensing element. The conductive liquid 125 can include, for example, one or more of mercury, gallium, indium, tin, nickel, copper and silver. The micro-channels can be connected to a sensing device, such as an ohmmeter, via leads 140.

In the embodiment of the invention shown in FIGS. 7A and 7B, the sensor 200 can be composed of two layers, completely bonded to each other. One layer being completely flat, and the other containing a high aspect-ratio, curved channel 220 forming a circular or polygonal shape. The channel 220 can be filled with eGaIn in the same way as described elsewhere herein. The channel in the bottom layer can be divided into three (or more) subchannels 220A by the connecting wires 230. When a shear stress is applied to the middle of the sensor, one or more of the subchannels 220A is compressed, reducing its cross-sectional area and resulting in its increased electrical resistance.

The embodiment of the invention shown in FIGS. 7A and 7B does not use a more rigid sensing element, thus enabling the sensor 200 to be completely soft. The sensor can be used to sense shear and strain as the portion of the channel 220 that is tangential to strain direction will become compressed and the electrical resistance in the subchannel 220A will increase. In addition, the sensor can be insensitive to normal pressure, e.g., the normal force applied to the middle of the sensor.

The sensor can be adapted for use with any device or method where it is useful to know whether a surface is being subjected to a force and the intensity and direction of such force. The sensor can be scaled upwardly and downwardly and can be adapted for numerous practical applications. The sensor can be used, for example, with consumer electronics, in research laboratories, for robotics and in manufacturing equipment and processes. Some specific applications for this sensor include wearable electronics for which surfaces are arbitrary and dynamic (that is, to measure pressures and stresses, e.g., on an athlete shoe's sole or motor vehicle tire tread).

Grip force measurement to estimate the correct force to hold an object, without letting it slip. In addition, other applications include use of the sensor with circuits printed on materials like plastic, cloth or paper; touch-sensitive control panels and gesture sensing; printed electronics; stretchable circuits; washable circuits; sports clothing; medical applications; toys; interactive fabrics; interactive paper; interactive displays and the like. Further, in the automotive industry, for example, the sensor can be used for traction control systems and in order to monitor forces applied to automobile tires.

The subject matter of the present invention can be defined by any of the following paragraphs:

A. A multi-axis sensor comprising:
 a layer of flexible material having a defined thickness and a contact surface;
 one or more substantially rigid sensing elements embedded within the flexible material, each sensing element including a substantially planar portion and at least one projecting portion extending substantially perpendicular to the planar portion, the planar portion being oriented substantially parallel to at least a portion of the contact surface;
 at least one microchannel in the flexible material extending near the planar portion of at least one of the rigid sensing elements, such that a force applied to the contact surface causes the rigid sensing element to move relative to the microchannel and cause the microchannel to change in a cross-sectional dimension; and
 a conductive fluid disposed in the at least one microchannel, wherein electrical resistance of the conductive fluid in the at least one micro channel changes as a function of the force applied to contact surface.

B. The multi-axis sensor according to paragraph A wherein the conductive fluid includes Eutectic Gallium Indium.

C. The multi-axis sensor according to paragraph A wherein the projecting portion of the rigid sensing element extends along a first axis and the flexible material includes a plurality of microchannels arranged around the first axis adjacent the planar portion of the at least one rigid sensing element such that a force applied to the contact surface causes the rigid sensing element to move relative to the microchannel and cause the microchannel to change in a cross-sectional dimension.

D. A sensor comprising:
a layer having viscoelastic properties, the layer comprising a void, the void filled with a fluid; and
a solid structure embedded within the layer,
wherein a force is applied to a top surface of the layer causes the solid structure to press into the void changing the shape of the void and causing a pressure of the fluid to change, and
wherein a direction and intensity of the force is determined by measuring a change of electrical resistance of the fluid.

E. The sensor of paragraph D, wherein the layer comprises an elastomer.

F. The sensor of paragraph D, wherein the layer comprises silicone rubber.

G. The sensor of paragraph D, wherein the fluid is a conductive liquid.

H. The sensor of paragraph G, wherein the conductive liquid is Eutectic Gallium Indium.

I. The sensor of paragraph D, wherein the solid structure comprises plastic.

J. The sensor of paragraph D, wherein the solid structure comprises a lower portion having a width greater than a height of the lower portion and an upper portion having a height greater than a width of the upper portion, wherein the upper portion has a vertical axis that is substantially parallel to a vertical axis of the lower portion and wherein the upper portion and the lower portion have horizontal cross sectional shapes that are circular or rounded.

K. The sensor of paragraph D, wherein the void comprises a plurality of microchannels radiating from a central axis.

L. The sensor of paragraph K, wherein the plurality of microchannels are continuously interconnected.

M. The sensor of paragraph K, wherein one of the plurality of microchannels terminates in a pad region adapted for connection to a lead.

N. The sensor of paragraph K, wherein two of the plurality of microchannels are connected to each other through a connecting region, wherein a size of the connecting region is greater than a size of each of the plurality of microchannels.

O. The sensor of paragraph K, wherein the void consists of twenty-four microchannels radiating from a central axis,
wherein at least one microchannel of the twenty-four microchannels is connected to a first terminating region having a predefined shape,
wherein at least one microchannel of the twenty-four microchannels is connected to a second microchannel of the twenty-four microchannels through a first connecting region having a predefined shape,
wherein at least one microchannel of the twenty-four microchannels is connected to a third microchannel of the twenty-four microchannels through a second connecting region having the predefined shape, and
wherein at least one microchannel of the twenty-four microchannels is connected to a second terminating region having a predefined shape.

P. The sensor of paragraph O, wherein the first terminating region has an area larger than the second terminating region.

Q. A method of forming a sensor, the method comprising:
forming a layer having viscoelastic properties, the layer comprising a void, the void filled with a fluid;
forming a solid structure; and
embedding the solid structure within the layer,
wherein a force is applied to a top surface of the layer cause the solid structure to press into the void changing the shape of the void and causing a pressure of the fluid to change, and
determining a direction and intensity of the force as a function of a change in electrical resistance of the fluid.

R. The method of paragraph Q, wherein the layer comprises an elastomer.

S. The method of paragraph Q, wherein the layer comprises silicone rubber.

T. The method of paragraph Q, wherein the fluid is a conductive liquid.

U. The method of paragraph T, wherein the conductive liquid is Eutectic Gallium Indium.

V. The method of paragraph Q, wherein the solid structure comprises plastic.

W. The method of paragraph Q, wherein the solid structure comprises a lower portion having a width greater than a height of the lower portion and an upper portion having a height greater than a width of the upper portion, wherein the upper portion has a vertical axis that is substantially parallel to a vertical axis of the lower portion and wherein the upper and lower portion have horizontal cross sectional shapes that are circular or rounded.

X. The method of paragraph Q, wherein the void comprises a plurality of microchannels radiating from a central axis.

Y. The method of paragraph X, wherein the plurality of microchannels are continuously interconnected.

Z. The method of paragraph X, wherein one of the plurality of microchannels terminates in a pad region adapted for connection to a lead.

AA. The method of paragraph X, wherein two of the plurality of microchannels are connected to each other through a connecting region, wherein a size of the connecting region is greater than a size of each of the plurality of microchannels.

BB. The method of paragraph 24, wherein the void consists of twenty-four microchannels radiating from a central axis,
wherein at least one microchannel of the twenty-four microchannels is connected to a first terminating region having a predefined shape,
wherein at least one microchannel of the twenty-four microchannels is connected to a second microchannel of the twenty-four microchannels through a first connecting region having a predefined shape,
wherein at least one microchannel of the twenty-four microchannels is connected to a third microchannel of the twenty-four microchannels through a second connecting region having a predefined shape, and
wherein at least one microchannel of the twenty-four microchannels is connected to a second terminating region having a predefined shape.

CC. The method of paragraph BB, wherein the first terminating region has an area larger than the second terminating region.

DD. The method of paragraph Q, wherein the solid structure is formed using a 3D printer.

EE. A multi-axis sensor comprising:
a layer of flexible material having a defined thickness and a contact surface;
at least one microchannel having a high aspect-ratio curved shape in the flexible material extending near the planar portion of at least one of the rigid sensing elements, such that a force applied to the contact surface causes the microchannel to change in a cross-sectional dimension; and
a conductive fluid disposed in the at least one microchannel, wherein electrical resistance of the conductive fluid in the at least one microchannel changes as a function of the force applied to the flexible material.

Although some of various drawings illustrate a number of logical stages in a particular order, stages which are not order dependent can be reordered and other stages can be combined or broken out. Alternative orderings and groupings, whether described above or not, can be appropriate or obvious to those of ordinary skill in the art of computer science. Moreover, it should be recognized that the stages could be implemented in hardware, firmware, software or any combination thereof.

The foregoing description, for purpose of explanation, has been described with reference to specific embodiments. However, the illustrative discussions above are not intended to be exhaustive or to be limiting to the precise forms disclosed. Many modifications and variations are possible in view of the above teachings. The embodiments were chosen and described in order to best explain the principles of the aspects and its practical applications, to thereby enable others skilled in the art to best utilize the aspects and various embodiments with various modifications as are suited to the particular use contemplated.

We claim:

1. A multi-axis sensor comprising:
a layer of flexible material having a defined thickness and a contact surface;
one or more substantially rigid sensing elements embedded within the flexible material, each sensing element including a substantially planar portion and at least one projecting portion extending substantially perpendicular to the planar portion, the planar portion being oriented substantially parallel to at least a portion of the contact surface;
at least one microchannel in the flexible material extending near the planar portion of at least one of the rigid sensing elements, such that a force applied to the contact surface causes the rigid sensing element to move relative to the microchannel and cause the microchannel to change in a cross-sectional dimension; and
a conductive fluid disposed in the at least one microchannel, wherein electrical resistance of the conductive fluid in the at least one microchannel changes as a function of the change in orientation of the rigid sensing element.

2. The multi-axis sensor according to claim 1 wherein the conductive fluid include Eutectic Gallium Indium.

3. The multi-axis sensor according to claim 1 wherein the projecting portion of at least the rigid sensing element extends along a first axis and the flexible material includes a plurality of microchannels arranged around the first axis adjacent the planar portion of the at least one rigid sensing element such that a force applied to the contact surface causes the rigid sensing element to move relative to the microchannel and cause the microchannel to change in a cross-sectional dimension.

4. A sensor comprising:
a layer having viscoelastic properties, the layer comprising a void, the void filled with a fluid; and
a solid structure embedded within the layer,
wherein, when a force is applied to a top surface of the layer, the solid structure presses into the void, changes the shape of the void and causes a pressure of the fluid to change, and
wherein a direction and intensity of the force is determined by measuring a change of the pressure of the fluid.

5. The sensor of claim 4, wherein the layer comprises an elastomer.

6. The sensor of claim 4, wherein the layer comprises silicone rubber.

7. The sensor of claim 4, wherein the fluid is a conductive liquid.

8. The sensor of claim 7, wherein the conductive liquid is Eutectic Gallium Indium.

9. The sensor of claim 4, wherein the solid structure comprises plastic.

10. The sensor of claim 4, wherein the solid structure comprises a lower portion having a width greater than a height of the lower portion and an upper portion having a height greater than a width of the upper portion, wherein the upper portion has a vertical axis that is parallel to or close to a vertical axis of the lower portion and wherein the upper and lower portion have horizontal cross sectional shapes that are circular or rounded.

11. The sensor of claim 4, wherein the void comprises a plurality of microchannels radiating from a central axis.

12. The sensor of claim 11, wherein the plurality of microchannels are continuously interconnected.

13. The sensor of claim 11, wherein one of the plurality of microchannels terminates in a pad region adapted for connection to a lead.

14. The sensor of claim 11, wherein two of the plurality of microchannels are connected to each other through a connecting region, wherein a size of the connecting region is greater than a size of each of the plurality of microchannels.

15. The sensor of claim 11, wherein the void consists of twenty-four microchannels radiating from a central axis,
wherein at least one microchannel of the twenty-four microchannels is connected to a first terminating region having a predefined shape,
wherein at least one microchannel of the twenty-four microchannels is connected to a second microchannel of the twenty-four microchannels through a first connecting region having a predefined shape,
wherein at least one microchannel of the twenty-four microchannels is connected to a third microchannel of the twenty-four microchannels through a second connecting region having the predefined shape, and
wherein at least one microchannel of the twenty-four microchannels is connected to a second terminating region having a predefined shape.

16. The sensor of claim 15, wherein the first terminating region has an area larger than the second terminating region.

17. A method of forming a sensor, the method comprising:
forming a layer having viscoelastic properties, the layer comprising a void, the void filled with a fluid;
forming a solid structure; and
embedding the solid structure within the layer,
wherein, when a force is applied to a top surface of the layer, the solid structure presses into the void, changes the shape of the void and causes a pressure of the fluid to change, and
wherein a direction and intensity of the force is determined by measuring the change of the pressure of the fluid.

18. The method of claim 17, wherein the layer comprises an elastomer.

19. The method of claim 17, wherein the layer comprises silicone rubber.

20. The method of claim 17, wherein the fluid is a conductive liquid.

21. The method of claim 20, wherein the conductive liquid is Eutectic Gallium Indium.

22. The method of claim 17, wherein the solid structure comprises plastic.

23. The method of claim 17, wherein the solid structure comprises a lower portion having a width greater than a height of the lower portion and an upper portion having a height greater than a width of the upper portion, wherein the upper portion has a vertical axis that is parallel to or close to a vertical axis of the lower portion and wherein the upper and lower portion have horizontal cross sectional shapes that are circular or rounded.

24. The method of claim 17, wherein the void comprises a plurality of microchannels radiating from a central axis.

25. The method of claim 24, wherein the plurality of microchannels are continuously interconnected.

26. The method of claim 24, wherein one of the plurality of microchannels terminates in a pad region adapted for connection to a lead.

27. The method of claim 24, wherein two of the plurality of microchannels are connected to each other through a connecting region, wherein a size of the connecting region is greater than a size of each of the plurality of microchannels.

28. The method of claim 24, wherein the void consists of twenty-four microchannels radiating from a central axis,
    wherein at least one microchannel of the twenty-four microchannels is connected to a first terminating region having a predefined shape,
    wherein at least one microchannel of the twenty-four microchannels is connected to a second microchannel of the twenty-four microchannels through a first connecting region having a predefined shape,
    wherein at least one microchannel of the twenty-four microchannels is connected to a third microchannel of the twenty-four microchannels through a second connecting region having a predefined shape, and
    wherein at least one microchannel of the twenty-four microchannels is connected to a second terminating region having a predefined shape.

29. The method of claim 28, wherein the first terminating region has an area larger than the second terminating region.

30. The method of claim 17, wherein the solid structure is formed using a 3D printer.

31. A multi-axis sensor comprising:
    a layer of flexible material having a defined thickness and a contact surface;
    at least one microchannel having a high aspect-ratio curved shape in the flexible material extending near the planar portion of at least one of the rigid sensing elements, such that a force applied to the contact surface causes the microchannel to change in a cross-sectional dimension; and
    a conductive fluid disposed in the at least one microchannel, wherein electrical resistance of the conductive fluid in the at least one microchannel changes as a function of the sheer stress applied to the flexible material adjacent the microchannel.

* * * * *